United States Patent [19]

Redemann

[11] Patent Number: 4,490,380
[45] Date of Patent: Dec. 25, 1984

[54] HALOPYRIDINE SULFONAMIDE AS INSECTICIDAL AGENTS

[75] Inventor: Carl T. Redemann, Walnut Creek, Calif.

[73] Assignee: The Dow Chemical Company, Midland, Mich.

[21] Appl. No.: 462,485

[22] Filed: Mar. 31, 1983

Related U.S. Application Data

[63] Continuation of Ser. No. 296,608, Aug. 26, 1981, abandoned.

[51] Int. Cl.$^3$ ............................................. A01N 43/40
[52] U.S. Cl. ................................................... 424/263
[58] Field of Search ......................................... 424/263

[56] References Cited

U.S. PATENT DOCUMENTS 3,821,216  6/1974  Domenico ........................... 424/263

FOREIGN PATENT DOCUMENTS 107422   5/1967  Denmark .
1293909 10/1972  United Kingdom .

OTHER PUBLICATIONS

DeMilo et al., J. Agric. Food Chem., vol. 25, No. 1 (1977), pp. 81–83.
Translation of Denmark Patent 107422.

Primary Examiner—Allen J. Robinson
Attorney, Agent, or Firm—S. Preston Jones; Ronald G. Brookens

[57] ABSTRACT

Disclosed is 3-chloro-2-pyridine sulfonamide, said compound being useful as an insecticide.

1 Claim, No Drawings

HALOPYRIDINE SULFONAMIDE AS INSECTICIDAL AGENTS

CROSS REFERENCE TO RELATED APPLICATION

This is a continuation of application Ser. No. 296,608 filed Aug. 26, 1981, now abandoned.

BACKGROUND OF THE INVENTION

This invention pertains to the novel compound 3-chloro-2-pyridine sulfonamide and its use as an insecticide for the control of various insects.

Halopyridine sulfonamides have been used as herbicides. See, for example, Tomlin et al., British Pat. No. 1,293,909, where compounds of the formulae

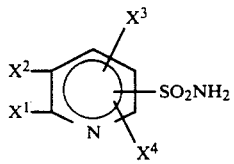

are discussed. At leat two of $X^1$–$X^4$ represent halogens, preferably fluoro or more especially chloro, and the remainder are selected from hydrogen, halogen, alkoxy, amino, alkylamino, arylamino, carboxy, carbalkoxy, hydroxy, mercapto, nitro and hydrocarbon substituents. In said disclosure, the sulfonamide group may be located at the 2, 3 or 4 position, however, the sulfonamide located at the 4 position is preferred.

SUMMARY OF THE INVENTION

The present invention is directed to the novel compound 3-chloro-2-pyridine sulfonamide which is represented by the formulae:

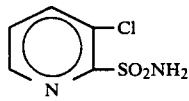

Said compound exhibits a wide range of insecticidal activity by controlling the growth and proliferation of various insects.

DETAILED DESCRIPTION OF THE INVENTION

An "insecticide" as used herein means a compound that controls the growth and proliferation of insects. The compound of the present invention is a broad-spectrum insecticide which can be used to control various insects during any stage of insect development, i.e. adult, larvae or egg. Due to its unique structure, the compound of this invention may be useful for the control of insects resistant to organic phosphate or to halogenated hydrocarbons.

The halopyridine sulfonamide of the present invention is prepared in a two-step process. In step one, benzyl mercaptan is dissolved in a solvent such as dimethylformamide or dimethylsulfoxide, mixed with 2,3-dichloropyridine and heated at about 50°–100° C. for about 2–6 hours. The residue is taken up in a solvent and distilled to give the resulting product, 3-chloro-2-(phenylmethyl)thio)pyridine. In step two, the halophenylmethylthiopyridine prepared in step one is converted by oxidative chlorination to a halopyridine sulfonyl chloride upon exposure to chlorine. The resulting sulfonyl chloride compound is reacted with aqueous ammonia for about 16 hours. The mixture is then acidified to a pH of about 5 and extracted with a suitable solvent, preferably ethyl acetate, and dried for 3–5 hours to yield the novel product, 3-chloro-2-pyridine sulfonamide. The product of the present invention is a colorless, needle-like, crystalline solid with a melting point of 128°–130° C. It is soluble in the usual organic solvents and in warm water.

EXAMPLE 1

Preparation-Step I

Preparation of 3-Chloro-2-((Phenylmethyl)thio)pyridine 42.0 Grams (0.338 mole) of benzyl mercaptan were dissolved in 350 ml dimethylformamide which had been dried over molecular sieves. The solution was placed under a nitrogen atmosphere and 16.2 grams (0.338 mole) of a 50 percent dispersion of sodium hydride was slowly added. Stirring was continued until hydrogen gas evolution stopped. Thereupon, the resulting solution was added slowly, again with stirring, to a solution of 50.0 grams (0.338 mole) of 2,3-dichloropyridine in 200 ml dry dimethylformamide. The mixture was heated at 70° C. for 4 hours.

The mixture was cooled to room temperature and removed from the solvent under reduced pressure. The pasty residue was taken up in methylene chloride and washed with water to remove sodium chloride and residual dimethylformamide. The solution was distilled under high vacuum (on the Kugel-Rohr at 120° C.) to obtain 70.0 grams of pale yellow oil, $N_D^{23}=1.6275$.

Preparation-Step II

Preparation or 3-Chloro-2-Pyridine Sulfonamide 53.0 Grams (0.225 mole) of 3-chloro-2-((phenylmethyl)thio)pyridine were added to 250 ml of acetic acid containing 16.2 grams (0.90 mole) of water. The mixture was cooled in an ice bath and passed in a stream of chlorine at 10°–15° C. for 3½ hours. The resulting cold acetic acid solution was poured, with stirring, into a mixture of 180 grams (2.2 moles) of sodium acetate, 500 ml water and 250 grams crushed ice. (The sodium acetate converts the 3-chloro-2-pyridine sulfonyl chloride present as the hydrochloride, into free 3-chloro-2-pyridine sulfonyl chloride.) The resulting mixture was extracted with methylene chloride, washed with water, and dried over anhydrous sodium sulfate. The methylene chloride extract was evaporated to 150 ml and cooled to −30° C. in a dry ice bath.

To the above extract was slowly added 100 ml of concentrated aqueous ammonia −30° C. and the mixture was stirred 16 hours. The phases which occurred were separated and the methylene chloride was re-extracted with concentrated ammonia. The ammonia extracts were combined and acidified to pH 5 with 12N hydrochloric acid. The pH solution was extracted with ethyl acetate, evaporated to dryness and recrystallized from chlorobenzene to obtain the 3-chloro-2-pyridine sulfonamide produced in a yield of 0.3 gram (0.7 percent of theoretical) of colorless needles melting at 127°–135° C. A further recrystallization from hot water afforded colorless needles melting at 128°–130° C.

In its use as an insecticide, an insecticidal amount of the compound per se or a composition incorporating an insecticidal amount of the compound is used as the toxicant for contact with the pest insect or its habitat. The insecticidal amount, of course, is that quantity which elicits toxic mortality among the treated pests. Generally, such insecticidal response results by contacting the target pests or their habitat with a composition containing from 0.00001 to 99 or more percent of the active compound in the total composition. Good results are achieved in the present invention upon contact with a composition containing up to about 600 parts of the active compound per million by weight.

Insecticidal activity is the ability of an insecticide to kill various insects and is expressed as a percentage of the number of insects killed relative to the number of insects exposed to the insecticide. Methods of applying the insecticide are discussed in the examples which are discussed later. Insecticidal activities of 3-chloro-2-pyridine sulfonamide are presented in Table I.

TABLE I

| Insect | Concentration of Insecticide in PPM by Weight | Percent Kill |
| --- | --- | --- |
| Two-spotted spider mite | 600 | 90 |
| Tobacco budworm | 600 | 100 |
| Tobacco budworm larvae | 480 | 100 |
| Leafhopper | 600 | 100 |
| House fly | 100 | 100 |

Suitable compositions include those which are in the form of liquid solutions, liquid emulsifiable concentrates, and dust or granular preparations. Such can be further diluted as and where appropriate with conventional diluents.

Liquid compositions containing the active compound are prepared by dissolving the active compound in a suitable inert organic solvent such as acetone, toluene, xylene, methylene chloride, chlorobenzene, ethyl ether or petroleum distillates or by dispersing the active compound in water with or without the aid of a suitable surface acting dispersing agent such as can be provided by ionic or nonionic dispersing and emulsifying agents.

The aqueous compositions may contain one or more water-immiscible solvents for the toxicants. In such compositions, the carrier comprises an aqueous emulsion, that is, a mixture of water-immiscible solvent, emulsifying agent and water. The choice of dispersing and emulsifying agents and the amounts thereof employed is dictated by the nature of the composition type and by the ability of the agent to facilitate the dispersion of the active toxicant compound in the aqueous carrier to produce the desired composition. Dispersing and emulsifying agents which may be employed in the compositions include the condensation products of alkylene oxides with phenols and organic acids, alkylarylsulfonates, polyoxyethylene derivatives or sorbitan esters, complex ether alcohols, mahogany soaps, and the like. In such compositions, the surface active agents are usually employed in the amount of from 1 to 20 percent by weight of the combined weight of the surface active agent and the active compound.

In the preparation of dust compositions, the active compound is dispersed in and on a finely divided inert solid such as talcum, chalk, gypsum, and the like. In such operations, the carriers are mechanically ground with the compounds or wet with a volatile organic solvent solution thereof. Similarly, dust compositions containing the compound may be prepared from bentonite, fuller's earth, attapulgite, and other clays. Depending upon the proportions of ingredients, these dust compositions may be employed as concentrates and subsequently diluted with additional solid surface acting dispersing agent or with talc, chalk, or gypsum and the like to obtain a desired amount of active agent in a composition adapted to be applied for insect control. Also, such concentrate dust compositions may be dispersed in water with or without the aid of a dispersing agent to form spray mixtures.

Granular formulations are conveniently prepared by impregnation, such as through simple mechanical mixing of the active compound in a pressurized carrier, usually of the type herebefore set forth.

In practice, the active compound is distributed so as to provide contact of the target insect with toxic amounts of the active compound. Such contact can be achieved through direct contact of the active compound with the target insect or by more indirect means such as by application to its food and/or habitat. Thus, for example, the active compound or a composition thereof can be spread throughout the environs of the target host so as to both provide direct and indirect contact thereof or bait compositions incorporating a toxic amount of the active compound or composition thereof can be readily prepared and strategically located so as to provide ultimate contact of the host species therewith.

The following examples serve to further typify the nature of the present invention and are given solely for the purpose of illustration.

EXAMPLE 2

25 Parts by weight of 3-chloro-2-pyridine sulfonamide, 60 parts of fuller's earth, 10 parts of diatomaceous earth, 3 parts of an alkyl aryl sulfonate (Naccanol NR) and 2 parts of a polymerized sodium salt of a substituted benzoid alkyl sulfonic acid (Daxad No. 27) are mechanically mixed and ground together to prepare a concentrate composition in the form of a wettable powder.

Similarly, 25 parts by weight of 3-chloro-2-pyridine sulfonamide, 65 parts xylene and 10 parts of a dimeric alkylated aryl polyether alcohol (Triton X-155) are mechanically mixed together to prepare a liquid emulsifiable concentrate composition.

In a like manner, 6 parts by weight of the 3-chloro-2-pyridine sulfonamide, 2 parts of Naccanol NR, 2 parts of Daxad No. 27, and 200 parts of water are ballmilled together to prepare a concentrate composition in the form of a water-dispersible liquid.

EXAMPLE 3

1 Part of 3-chloro-2-pyridine sulfonamide is mixed with 99 parts of purified kerosene to obtain an oil preparation having an active ingredient concentration of 1 percent. In application, the composition can be atomized or sprayed as is.

The concentrate compositions may be further diluted in their concentrate state and/or dispersed in water to prepare aqueous compositions which have desirable wetting and penetrating properties. These compositions are adapted to be employed to treat target insects and distribute the active compound in insecticidal concentrations.

EXAMPLE 4

In this operation, an aqueous dispersion was prepared by admixing a predetermined amount of 3-chloro-2-pyridine sulfonamide dissolved in a suitable inert solvent, with a predetermined quantity of water and a predetermined amount of a surfactant to give aqueous dispersions containing varying predetermined amounts of the compound as the sole active toxicant. Separate 3 inch discs cut from tobacco plant leaves were thoroughly wetted by briefly dipping into one of the dispersions and the wetted leaves placed in an open Petri dish and permitted to dry. After the leaves were dry, 5 live tobacco budworm larvae, approximately late 2nd instar, were placed in each Petri dish. In identical operations, 5 like live tobacco budworm larvae were placed in control Petri dishes, the leaf therein having been wetted with a solution containing only water and surfactant. The dishes were maintained under moist conditions at about 80° F., conducive for the growth of the tobacco budworm larvae, for a period of about 2 days. At the end of the 2-day period, the dishes were examined to determine the ability of the insecticide to kill said insects.

EXAMPLE 5

Aqueous dispersions were prepared by admixing a predetermined amount of 3-chloro-2-pyridine sulfonamide dissolved in a suitable inert solvent, with a predetermined quantity of water and a predetermined amount of a surfactant to give aqueous dispersions containing varying predetermined amounts of the compound as the sole toxicant. Tobacco budworm adults were placed on separate tobacco seedlings and left on for one day. This permitted the budworms to lay eggs. One group of the seedlings was sprayed with one of the dispersions to run off. In like manner, another group of the seedlings was sprayed to run off with a solution containing only water and surfactant. The seedlings were maintained under conditions conducive to the growth of the seedlings and tobacco budworms. After a period of two days, the seedlings were examined to determine the ability of the insecticides to kill said insects.

EXAMPLE 6

Aqueous dispersions were prepared by admixing a predetermined amount of 3-chloro-2-pyridine sulfonamide dissolved in a suitable inert solvent, with a predetermined quantity of water and a predetermined amount of a surfactant to give aqueous dispersions containing varying predetermined amounts of the compound as the sole toxicant. Separate cotton plants were infested with approximately 100 two-spotted spider mites and the plants dipped into one of the dispersions. In a like manner, approximatley 100 two-spotted spider mites were placed on control plants and the plants sprayed to run off with a solution containing only water and surfactant. The plants were maintained under conditions conducive to the growth of the plants and mites. After a period of five days, the plants were examined to determine the ability of the insecticide to kill said insects.

What is claimed is:

1. A method for killing insects which comprises contacting said insects or their habitat with an insecticidally effective amount of a composition containing, as the active ingredient, 3-chloro-2-pyridine sulfonamide in intimate admixture with an insecticidally acceptable inert carrier therefor.

* * * * *